(12) United States Patent
de Vries et al.

(10) Patent No.: US 9,560,991 B2
(45) Date of Patent: Feb. 7, 2017

(54) EFFICIENT EVALUATION OF HEARING ABILITY

(75) Inventors: Aalbert de Vries, Eindhoven (NL); Svante Sten Johan Stadler, Stockholm (SE); Arne Leijon, Stockholm (SE); Tjeerd Maarten Hein Dijkstra, Utrecht (NL); Alexander Ypma, Veldhoven (NL)

(73) Assignee: GN HEARING A/S, Ballerup (DK)

( * ) Notice: Subject to any disclaimer, the term of this patent is extended or adjusted under 35 U.S.C. 154(b) by 1271 days.

(21) Appl. No.: 12/429,783

(22) Filed: Apr. 24, 2009

(65) Prior Publication Data
US 2010/0257128 A1 Oct. 7, 2010

(30) Foreign Application Priority Data

Apr. 6, 2009 (EP) ..................................... 09388009

(51) Int. Cl.
G06F 15/18 (2006.01)
A61B 5/12 (2006.01)
G06N 99/00 (2010.01)
H04R 25/00 (2006.01)
A61B 5/0484 (2006.01)

(52) U.S. Cl.
CPC ............. A61B 5/121 (2013.01); G06N 99/005 (2013.01); H04R 25/70 (2013.01); A61B 5/04845 (2013.01)

(58) Field of Classification Search
None
See application file for complete search history.

(56) References Cited

U.S. PATENT DOCUMENTS

| 5,937,384 | A | * | 8/1999 | Huang et al. ................. 704/256 |
| 6,496,585 | B1 | | 12/2002 | Margolis |
| 6,574,342 | B1 | | 6/2003 | Davis et al. |
| 6,602,202 | B2 | * | 8/2003 | John et al. ..................... 600/559 |
| 7,424,463 | B1 | * | 9/2008 | Napoletani et al. ............ 706/20 |
| 2008/0221719 | A1 | | 9/2008 | Margolis et al. |
| 2010/0174540 | A1 | * | 7/2010 | Seefeldt ........................ 704/224 |

FOREIGN PATENT DOCUMENTS

| EP | 1933591 | 6/2008 |
| WO | 0187147 | 11/2001 |
| WO | 2007 043043 | 4/2007 |

OTHER PUBLICATIONS

Asha, Guidelines for Manual Pure-Tone Threshold Audiometry, web access at http://www.asha.org/docs/html/GL2005-00014.html, 2005.

(Continued)

*Primary Examiner* — Kakali Chaki
*Assistant Examiner* — Luis Sitiriche
(74) *Attorney, Agent, or Firm* — Vista IP Law Group, LLP

(57) ABSTRACT

A system for establishing a hearing ability model of a hearing ability of a person, includes a data storage configured to store a representation of a distribution of a hearing ability of a population of individuals, and a processor configured to establish a hearing ability model representing a hearing ability of the person based at least in part on (i) information regarding a person's response to a stimulus of a hearing evaluation event, and (ii) the representation of the distribution of the hearing ability of the population.

41 Claims, 5 Drawing Sheets

(56) References Cited

OTHER PUBLICATIONS

British Society of Audiologist Recommended Procedure: Pure tone air and bone conduction threshold audiometry with and without masking and determination of uncomfortable loudness levels http://www.thebsa.org.uk/docs/RecPro/PTA.pdf 2004.
Ozdamar O, Eilers RE, Miskiel E, Widen JE.; "Classification of audiograms by sequential testing using a dynamic Bayesian procedure"; Journal of the Acoustical Society of America; 1990; 88:2171-9.
Stifenhofer, G. Woods et al.; "Absolute detection results with a Bayesian adaptive tracking procedure using simulated and human subjects"; Journal of the Acoustic Society of America; 2007; 121(5):3196 (A). Poster available at http://starkeyresearch.com/pdfs/PosterASA 28052007.pdf.
European Search Report for EP09388009 dated Sep. 17, 2009.
Rubin, Timothy N. et al., "Hierarchical Bayesian Modeling of Individual Differences in Texture Discrimination", Department of Congnitive Sciences, University of California, 6 pages.
Communication pursuant to Article 94(3) EPC dated Jul. 29, 2015, for corresponding European Patent Application No. 09 388 009.4, 3 pages.

\* cited by examiner

EFFICIENT EVALUATION OF HEARING ABILITY

RELATED APPLICATION DATA

This application claims priority to and the benefit of European Patent Application No. 09388009.4, filed on Apr. 6, 2009, the entire disclosure of which is expressly incorporated by reference herein.

FIELD

The present application relates to a method of establishing a hearing ability model for a person and a system for establishing a model of the hearing ability for a person.

BACKGROUND & SUMMARY

When a person needs a hearing aid, the hearing aid should be configured to the specific hearing ability of that person. Specifically the hearing ability may include hearing loss. There are several ways of determining the hearing ability of a person. The most common method is pure-tone audiometric for determining hearing thresholds at selected frequencies. A model may then be established using the measurement results. Also hearing ability of a person without a hearing loss may be determined so as to improve or enhance hearing for that person.

The threshold of hearing is one of the most important clinical variables for characterizing a person's hearing ability profile, since it indicates the weakest acoustic signal that the person is able to hear. Specifically the person's hearing ability profile may provide information on the weakest acoustic signal a person is able to hear as a function of frequency. Because hearing ability, and specifically hearing loss, results may have significant influence on educational, occupational, social, and/or psychological outcome it is advantageous that procedures may be standardized and consistent among test providers. Since early days, starting with Fechner's method of limits, several pure-tone audiometric measurement procedures have been proposed to estimate a person's hearing threshold.

Three general methods of pure tone audiometry are used namely (a) manual audiometry, (b) automatic audiometry, also known as Békésy audiometry; and (c) computer-assisted audiometry.

Békésy audiometry refers to a method where the listener himself controls the loudness of a frequency-sweeping stimulus so as to follow his own hearing threshold as close as possible. Manual threshold measurement procedures put the audiologist in control of the stimulus presentation schedule. The currently recommended manual pure-tone threshold estimation method relies on an ascending technique with 5 dB up and 10 dB down steps, (see the ASHA Guidelines for manual pure-tone threshold audiometry, 2005). Lately, computer-assisted procedures that implement popular manual and automatic procedures have become commercially available, such as the MADSEN Astera.

In addition to pure tone audiometry with a manual yes/no response, given e.g. as a sign to an audiologist or as a press on a button, indicating the ability of the person tested to hear a tone, variations of testing the hearing ability of a person exist both in the type of stimulation and in the observation of responses.

Sound transmitted in one ear may be conducted in the cranium bone and may be heard in the other ear, especially in the case where the hearing loss differs very much between the ears. In this case the stimulus may be required to comprise additional masking noise in the ear not tested, which is intended to reduce the risk of the person tested responding to sound transmitted to the other ear. To provide diagnosis of the source of a hearing loss, stimulus may also be transmitted via bone conduction as vibration rather than as air conducted sound. In this case masking becomes even more relevant. In the case of masked pure tones, the power level of the masking noise must be balanced correctly. Therefore such a masked test of hearing ability will have a longer duration.

In addition to using pure tones as stimulus, a combination of speech and noise may also be used to identify the speech hearing and/or speech recognition ability of the person tested. In this case the response may also be more complex in choosing between several potential words.

Especially for infants, unable to respond by pressing a button, recording responses in the form of the electrical potential measured on the scalp of a person tested (e.g. EEG) is also used as observations of responses. Various variations of this concept exist, for instance ABR (auditory brainstem response)—where an audiologist manually observes whether a curve shows a response to either click sounds for a simple evaluation of hearing ability, or alternatively whether the curve shows a response to pure tone stimulus similar to that in normal pure tone audiometry with the aim of estimating frequency dependent hearing thresholds, also ASSR (auditive steady state response) where frequency and/or amplitude modulated tone stimulus is correlated to responses in the form of EEG curves by statistical techniques.

Patent publication WO2007/042043 to GN ReSound provides information relating to Bayesian statistics background.

Ozdamar et al. (Journal of the Acoustical Society of America, 1990; 88:2171-9), proposed CAST (classification of audiograms by sequential testing) developed as an automated approach to screening infant hearing abilities using a modified Bayesian method. In contrast to the embodiments described herein, the CAST method is based on traditional recording of an audiogram, and after the test categorizing this according to a predefined discrete set of template audiograms. Furthermore, a new audiogram is assigned a posterior membership to a set of template audiograms incrementally.

A first aspect of the embodiments described herein relates to a method of establishing a hearing ability model for a person. The method may include providing a representation of the distribution of hearing ability for a population of individuals and the method may comprise the steps:
  i) performing a hearing evaluation event, comprising a stimulus of a person tested and a conscious or subconscious response of the person tested,
  ii) registering an observation related to the response of the hearing evaluation event,
  iii) establishing a hearing ability model representing the hearing ability of the person tested, based on the observation related to the hearing evaluation event and the representation of the distribution of the hearing ability.

Surprisingly the method above provides a model of the hearing ability of a person significantly faster than other methods as will be discussed below. In addition to that the method may provide an associated uncertainty of the model. The term faster may be construed as a shorter period of time where person is under active testing. The term faster may be also construed as a lower number of hearing evaluation events. One objective is to provide a method where the person is subjected to less discomfort while performing a hearing ability evaluation test.

The response of the person may be conscious and/or subconscious. E.g. the person may operate a switch and/or an electric signal in/from the brain may be registered.

The model may comprise an initial step of determining an initial model based on the representation of the distribution of hearing ability for a population of individuals and the first iteration of the method may include determining hearing ability model representing the hearing ability of the person tested based on the observation related to the hearing evaluation event and the initial model. Each subsequent iteration may include determining an updated model based on the latest hearing ability model and the latest, or set of latest, observations.

One object of the embodiments is to establish a sufficiently accurate estimate of the hearing threshold while limiting the burden on the person tested and/or the audiologist. In practice, this means that the "true" hearing threshold should be reached through a minimal number of listening experiments.

A second aspect of the present embodiments relates to a system for establishing a hearing ability model of the hearing ability of a person. The system may comprise:
- a data storage configured to store a representation of the distribution of the hearing ability of a population of individuals representing distribution of hearing ability of a multitude of hearing impaired individuals,
- a hearing evaluation device configured to provide a stimulus relating to a hearing evaluation event,
- an observation registering device configured to register a response related to the hearing evaluation event,
- a processor configured to establish a hearing ability model of the person tested based on the response related to the hearing evaluation event and the data set.

As with the above method the system according to the second aspect surprisingly provides a model of the hearing ability of a person by using few hearing evaluation events compared to other methods. This is contemplated to reduce the discomfort for a person being tested. This may be advantageous for any person and in particular, but not limited to, children and elderly persons. Other advantages will be obvious from the description below.

Further, the distribution of the hearing ability of a population of individuals may be stored as a data set or as a mathematical model or in any other appropriate way.

In accordance with some embodiments, a method of establishing a hearing ability model for a person using a representation of a distribution of hearing ability for a population of individuals, includes obtaining information regarding a person's response to a stimulus of a hearing evaluation event, and establishing, using a processor, a hearing ability model representing a hearing ability of the person, based at least in part on the information and the representation of the distribution of the hearing ability for the population.

In accordance with other embodiments, a system for establishing a hearing ability model of a hearing ability of a person, includes a data storage configured to store a representation of a distribution of a hearing ability of a population of individuals, and a processor configured to establish a hearing ability model representing a hearing ability of the person based at least in part on (i) information regarding a person's response to a stimulus of a hearing evaluation event, and (ii) the representation of the distribution of the hearing ability of the population.

In accordance with other embodiments, a system for establishing a hearing ability model of a hearing ability of a person, includes a data storage configured to store a representation of a distribution of a hearing ability of a population of individuals, a response observation device configured provide information regarding a person's response to a stimulus of a hearing evaluation event, and a processor configured to establish a hearing ability model representing a hearing ability of the person based at least in part on the information and the representation of the distribution of the hearing ability of the population.

In accordance with other embodiments, a system for establishing a hearing ability model for a person using a representation of a distribution of hearing ability for a population of individuals, includes means for obtaining information regarding a person's response to a stimulus of a hearing evaluation event, and means for establishing a hearing ability model representing a hearing ability of the person, based at least in part on the information and the representation of the distribution of the hearing ability for the population.

DESCRIPTION OF THE DRAWING FIGURES

The embodiments will now be described on more detail with reference to the appended figures. These drawings depict only typical embodiments and are not therefore to be considered limiting in scope.

DETAILED DESCRIPTION

Figure 1:
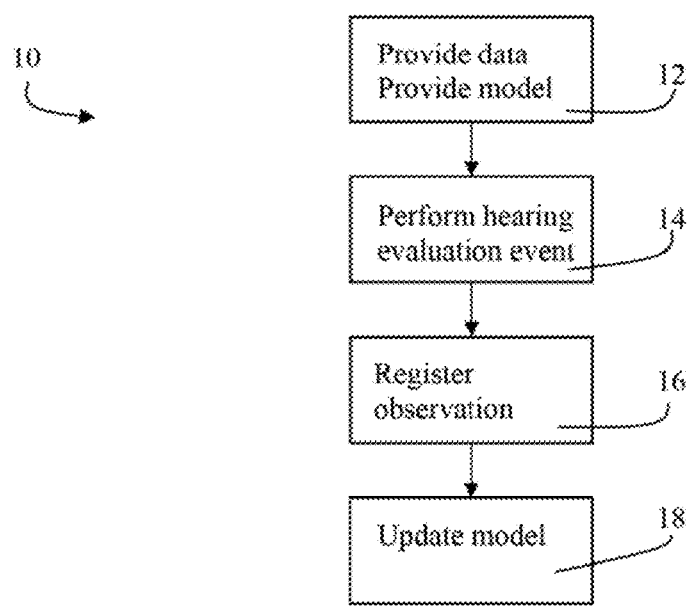
FIG. 1 is a schematic illustration of an embodiment of a method.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

In pure-tone audiometry, a sequence of N tones $(s_1, s_2, K, s_N)$ is presented at selectable frequency and power levels and the person tested is asked after each presentation if he or she hears the stimulus. Each stimulus presentation $s_n$ and associated response $r_n$ from the person tested is termed a hearing evaluation event, for which data is recorded or collected in a variable $d_n = \{s_n, r_n\}$. Using the data from a sequence of hearing evaluation events, termed an experiment $D = \{d_1, K, d_N\}$, an estimate x of the "true" hearing thresholds of the person tested, where x is defined as a K-dimensional variable $x = (x_1, K, x_K)^T$ with index k running for instance over the frequencies 250, 500, 1000, 2000, 3000, 4000, 6000 and 8000 Hz, may be established.

One way of optimizing the method used to establish the model is the determination or estimation of a proper stimulus sequence, i.e. a series, or just the next, of frequency and power levels of pure-tone stimuli, so as to reduce the uncertainty regarding the hearing thresholds as quickly as possible, i.e. using the lowest possible number of hearing evaluation events. The next preferred stimulus may be determined after each hearing evaluation event, and also several preferred candidates of hearing evaluation events may be determined.

The optimization may be established under provision of a representation of the probabilities of hearing thresholds. The representation may be provided prior to the testing as access to a data set of hearing abilities of a population or as a mathematical model taking the form as described in the following and be used to establish an estimate of the most probable K-dimensional value of x. In an advantageous embodiment the representation may also be used to determine the hearing evaluation event which will contribute the most to the reduction of the uncertainty of the K-dimensional value of x, or in other terms which hearing evaluation event will contribute with the highest marginal information gain.

In the case of determination of a hearing threshold audiogram by pure tone audiometry the hearing evaluation event corresponds to a combination of a stimulus characterized by a frequency and power level, and a response, i.e. whether the stimulus is heard.

FIG. 1 schematically illustrates a method 10 of establishing a hearing ability model for a person. The method 10 includes the step of providing a representation of the distribution of hearing ability for a population of individuals 12. The method further comprises the steps i) performing a hearing evaluation event 14, ii) registering an observation related to the hearing evaluation event 16, and iii) establishing a hearing ability model representing the hearing ability of the person tested, based on the observation of a response related to the hearing evaluation event and the representation of a population 18. Further the step 12 may include providing previously recorded data relating to the person tested, e.g. previously observed responses to hearing evaluation events, age and/or gender etc.

As mentioned above the step iii) denoted 18 in FIG. 1 may include establishing a hearing ability model representing the hearing ability of the person tested, based on the observation of a response related to the hearing evaluation event and a previously determined hearing ability model. Thereby the hearing ability model may be updated with the latest observation. This is sometimes referred to as learning.

Figure 2:
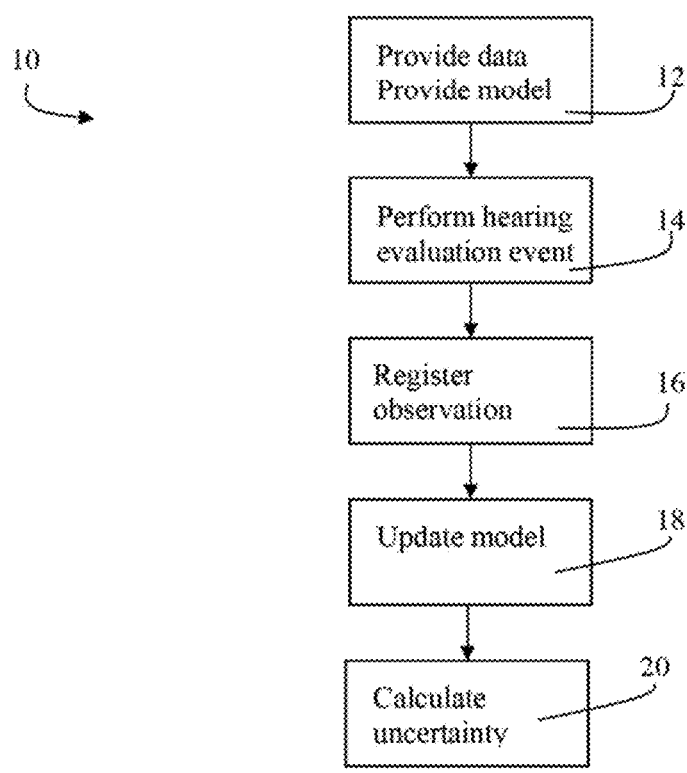
FIG. 2 is a schematic illustration of an embodiment of a method.

FIG. 2 schematically illustrates an embodiment of the method 10 of FIG. 1 further including a step 20 where an uncertainty is calculated. The uncertainty relates to the model and provides an indication to the operator, e.g. an audiologist, how certain, or uncertain, the model is. Based on this uncertainty the operator may decide if more observations are needed or if the model is sufficient. Further, a system may assist the operator in making this decision provided one or more stop criteria are provided, e.g. a threshold for the uncertainty or the like.

Figure 3:
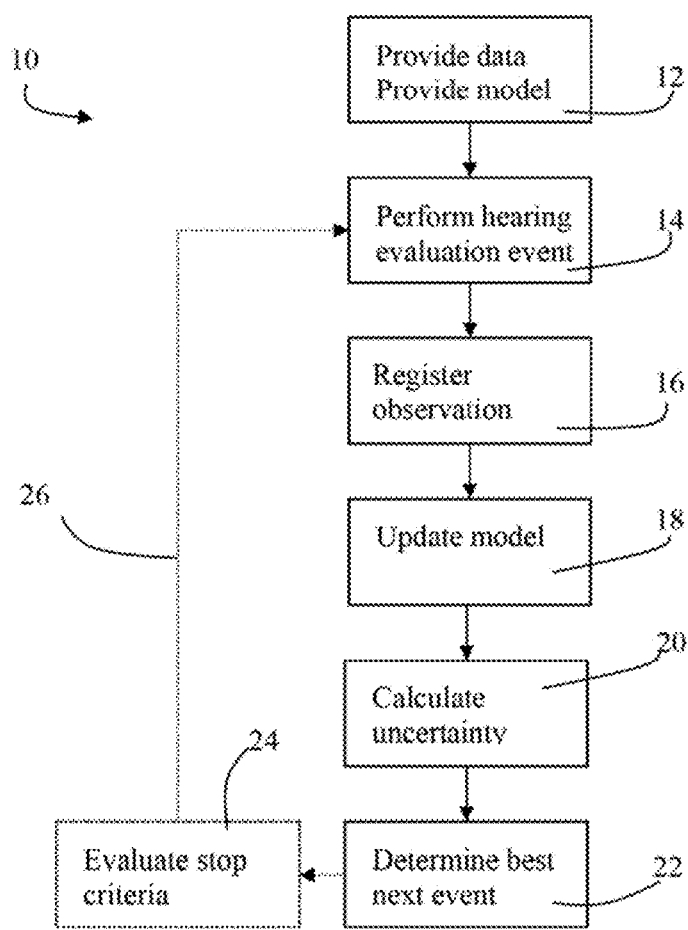
FIG. 3 is a schematic illustration of an embodiment of a method.

FIG. 3 schematically illustrates the method 10 of FIGS. 1 and 2 further comprising a step 22 where the event, that is contemplated to be the most beneficial, e.g. reducing the uncertainty most, is determined. In a presently preferred embodiment a system including a display device is configured to graphically display the model and uncertainties. The system may further be configured to display the best next event to an operator. Still further the system may be configured to display a plurality of preferred events to the operator.

Also illustrated in FIG. 3 is the optional step of evaluating stop criteria 24. If the criteria are met, the loop illustrated in FIG. 3 is stopped. If the criteria are not met the steps 14 through 22 are repeated.

In the following it will be demonstrated how the method may be implemented. The determination of a hearing threshold audiogram by pure tone audiometry will be used as an example, but the broader scope of the invention, as it also applies to other types of hearing evaluation events, including different stimuli and responses, must be bourn in mind. This will also be illustrated by further embodiments.

One object is to provide the stimulus sequence $(s_1, s_2, K, s_N)$ that leads to minimal (expected) uncertainty about the thresholds x. An important element in any effective pure-tone threshold estimation procedure is the availability of an estimate of the uncertainty of the estimated threshold. The estimate of the uncertainty of the estimated threshold is contemplated to provide the operator with information that may allow the operator to evaluate if further stimulus is required in order to establish whether the model sufficiently describes the hearing ability of the person tested.

The general mathematical treatment of uncertainty involves probability distributions, or probability densities in case of continuous-valued variables. For instance, our degree of belief that the hearing threshold x lies between the values $x_0$ and $x_0 + \delta x$ may be expressed by a probability mass $$\int_{x_0}^{x_0 + \delta x} p(x) dx$$

where the probability density function p(x) represents the state of knowledge regarding such beliefs over all possible values (the "domain") of x.

The present embodiments are based on the availability of a data set of hearing abilities for a group of persons, with a certain similarity to the person tested. From this data set a representation of the hearing abilities for a population (in its statistical sense i.e. a defined group of individuals) is provided,—either by looking up values in a database comprising the dataset, or by establishing a mathematical model of the hearing ability of the population (in the following "a population model"). In the case where a mathematical model is established, this may be done by any appropriate regression method, and the mathematical population model may be either nonparametric, such as a neural network, or the model may be parametric. For a parametric model several possibilities exist, including the preferred group of functions—cumulative density functions. A Gaussian cumulative density function may be chosen for a population model of hearing thresholds, as they are assumed to follow a normal distribution, but for other parameters, other appropriate cumulative density functions may also be chosen.

The following example will relate to a probabilistic model for hearing thresholds $p(x|\theta)$ where x refers to the hearing thresholds and $\theta$ to the model parameters. Such a model for the hearing threshold may refer to a Gaussian mixture model of the form $$p(x|\theta) = \sum_{k=1}^{K} \pi_k N(x|\mu_k, \Sigma_k).$$

In this case, the model parameters consist of the set $\theta=\{\pi_k,\mu_k,\Sigma_k: k=1,K,K\}$, where $\pi$ is a scaling factor, and $\mu$ and $\Sigma$ correspond to mean value and covariance matrix where the subscripts are indices for the tested frequencies. Alternative probabilistic model choices, including a Gaussian process model or polynomial regression model are also possible. Prior to any experiments, our state of knowledge about proper values for the hearing threshold model parameters is represented by a distribution $p(\theta)$. Usually, we take a uniform or Gaussian distribution with large variance for $p(\theta)$.

Given the database of hearing threshold measurements, it is possible to update our knowledge about the hearing threshold model parameters (20). Technically, this is most accurately implemented by Bayes rule, i.e.

$$p(\theta|D_n) \propto p(d_n|\theta) \cdot p'(\theta|D_{n-1})$$

The expression $p(\theta|D_n)$ should be interpreted as our state-of-knowledge about probable values for $\theta$, given the data $D_n$.

With updated model parameters, it is now possible to update our knowledge about the probability densities $p(x|D_n)$ for the hearing thresholds, given the data $D_n$.

Technically this is appropriately executed through a variant of the sum rule, also known as marginalization, as indicated in the algorithm.

$$p(x|D_n) = \int p(x|\theta) \cdot p(\theta|D_n) d\theta$$

At this stage an updated estimate of the audiogram is available, providing combined knowledge of the most likely values $x_n$, and an associated measure of uncertainty $\lambda_n$. A useful measure is the statistical entropy, $(\lambda_n = H|x|D_n| = E|-\log p(x|D_n)|)$, which is a general measure of uncertainty. Alternatively, computationally simpler measures such as the trace of the covariance matrix of x would also suffice.

From the updated estimate of the audiogram uncertainty, $\lambda_n$, a decision is established whether the uncertainty is satisfactory, in which case the audiogram is considered the final value and the test is completed, or whether a next hearing evaluation event must be carried out.

In case the stopping criterion has not (yet) been met, we will carry out another hearing evaluation event, i.e. present another pure-tone stimulus to the person tested, with registration of response.

If testing continues the candidates for the next hearing evaluation event must be selected. This is done in consideration of the values of an objective function, which may be $\lambda_{n+1}$, i.e. the expected uncertainty after the next hearing evaluation event. The set of possible frequencies and power levels defines the set of possible next stimuli. Having access to the full probability distribution $p(x|D_n)$ for the thresholds, makes it possible to select the stimulus s* from the set of all possible stimuli that provides the largest expected information gain (reduction of uncertainty). In particular, let $\lambda_{n+1}(d,s) = H|x|d,D_n|$ Hold the uncertainty estimate about the hearing thresholds, given audiometric observations $D_n$ and d. The expected information gain for a stimulus $s_{n+1}$ is then $$\lambda_{n+1}(s) = \sum_d p(d|s, D_n) H[x|d, D_n].$$

The best next stimulus, in the sense that it maximizes the expected information gain, is then given by $$s^*_{n+1} = \arg\min_s \lambda_{n+1}(s)$$

(i.e. the s which provides the lowest $\lambda_{n+1}$). $s_{n+1}*$ may in some cases be evaluated analytically, but typically it will be identified numerically by multiple evaluations of the objective function $\lambda_{n+1}(s)$. To reduce the calculation time, a local minimum may be accepted or a limited number of $\lambda_{n+1}(s)$ may be evaluated.

Figure 4:
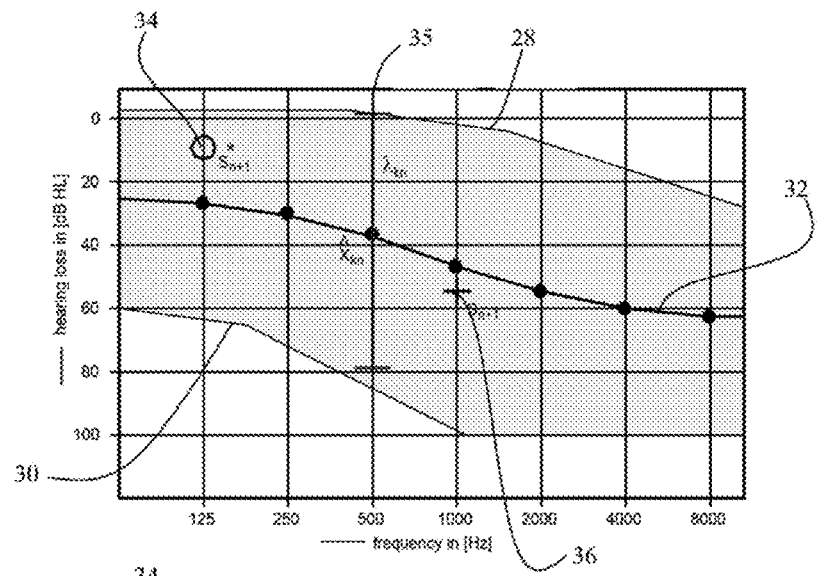
FIG. 4 is a schematic illustration of an audiogram.

Depending on the preferences, either a single preferred s or a ranked list of several candidates providing a high expected information gain may be presented to the audiologist (70). The presentation may either be as a list of possible (or preferred) stimuli, or graphically in an informed audiogram as shown in FIG. 4.

After this presentation the audiologist may choose the next stimulus—either by accepting a proposed value, by choosing from a list or by overriding the proposals of the method.

The last step of the method will then be the observation of a person tested response, $r_{n+1}$, to a stimulus, which in pure tone audiology is a yes/no answer, but in other hearing tests may be a more complex response, which must be decoded before the overall hearing event may be stored as a new data point $d_{n+1} = (r_{n+1}, s_{n+1})$, and be used for updating the probability distribution for the parameters $\theta$.

One embodiment of a method for establishing a model for hearing ability may be described by the following pseudo-code:

```
Procedure BIPTA:
 1. PROVIDE: a person tested
 2. PROVIDE: a hearing threshold model proposal p(x|θ) with prior p(θ)
 3. PROVIDE: a population database D_c
 4. INITIALIZE: n = 0; d_0 = D_c; p(θ|D_{-1}) = p(θ)

5. REPEAT
 6.   update model: p(θ|D_n) ∝ p(d_n|θ) · p(θ|D_{n-1})
 7.   update hearing threshold probability density function:
        p(x|D_n) = ∫ p(x|θ) · p(θ|D_n)dθ
 8.   compute mean hearing threshold estimate: x̂_n = E|x|D_n|
 9.   compute uncertainty: λ_n = H|x|D_n|
10.   IF stop_criterion is met
11.     RETURN: x̂_n, λ_n
12.   ELSE
13.     compute best next stimulus s*_{n+1} = arg min_s λ_{n+1}(s)
14.     Display informed-Audiogram iA(x̂_n, λ_n, s*_{n+1})
15.     audiologist chooses next stimulus: s_{n+1}
16.     record person tested response r_{n+1} and data d_{n+1} = (r_{n+1}, s_{n+1})
17.     n = n + 1
18.   ENDIF
19. FOREVER
```

Each step is described below in more detail.
1. PROVIDE: a person tested
   The person for whom the hearing thresholds is about to be measured is provided. The test to be performed is a pure-tone audiometric test.
2. PROVIDE: a hearing threshold model proposal p(x|θ) with prior p(θ)

We denote a probabilistic model for hearing thresholds by $p(x|\theta)$ where x refers to the hearing thresholds and $\theta$ the model parameters. In a typical embodiment, such a model for the hearing threshold refers to a Gaussian mixture model of the form $$p(x|\theta) = \sum_{k=1}^{K} \pi_k N(x|\mu_k, \Sigma_k).$$

In this case, the model parameters comprise the set $\theta=\{\pi_k, \mu_k, \Sigma_k : k=1, K, K\}$. Prior to any experiments, our state of knowledge about proper values for the hearing threshold model parameters is represented by a distribution $p(\theta)$, which usually, is uniform or Gaussian with large variance for $p(\theta)$.

3. PROVIDE: a population database $D_c$
Furthermore, preferably access to a database of previously measured hearing thresholds and other relevant measurements from other persons is provided. This data base will be referred to as the variable $D_c$, where the subscript 'c' indicates that the data relates to the 'community' i.e. the population.

4. INITIALIZE: $n=0$; $d_0=D_c$; $p(\theta|D_{-1})=p(\theta)$
Before the loop begins, the hearing evaluation event index n is set to zero, and the variables $d_n$ (data) and $p(\theta|D_{n-1})$ are initialized.

5. REPEAT
Begin the experimental loop 6. update model: $p(\theta|D_n) \propto p(d_n|\theta) \cdot p(\theta|D_{n-1})$
Given the database of hearing threshold (population) measurements, it is possible to update our knowledge about the hearing threshold model parameters, in the first instance the model is based on the population data alone, in the following the model is based on the population data and one or more previous measurements. Technically, this is most accurately implemented by Bayes rule $p(\theta|D_n) \propto p(d_n|\theta) \cdot p(\theta|D_{n-1}).$ The expression $p(\theta|D_n)$ should be interpreted as our state-of-knowledge about probable values for $\theta$, given the data $D_n$.

7. update hearing threshold probability density function:

$p(x|D_n) = \int p(x|\theta) \cdot p(\theta|D_n) d\theta$

With updated model parameters, it is now possible to update the knowledge about the probability densities $p(x|D_n)$ for the hearing thresholds given the data $D_n$. This may be executed using a variant of the sum rule, also known as marginalization.

8. compute expected hearing threshold: $\hat{x}_n = E[x|D_n]$
The expected values $\hat{x}_n = E[x|D_n] = \int x\, p(x|D_n)\,dx$ provide a good vector estimate for the hearing thresholds of the person tested, based on the population data. Note that we can make an estimate of the person tested hearing thresholds, even before any measurements on the person tested were administered.

9. compute uncertainty: $\lambda_n = H[x|D_n]$
Of course, the distribution $p(x|D_n)$ also reflects any uncertainty that we have about the thresholds of the person tested. We summarize this by a scalar measure $\lambda_n$ such as the statistical entropy $H[x|D_n] = E[-\log p(x|D_n)].$ 10. IF (stop criterion is met)

11. RETURN: $\hat{x}_n, \lambda_n$
At this point, we invoke a stopping criterion. Proper stopping criterions include the following:
Check if the duration of the experiment has surpassed a time limit
Alternatively, if the uncertainty measure $\lambda_n$ is smaller than a preset threshold, we might want to stop the procedure as well. After all, there's no point for more experimentation it we are certain enough about our hearing threshold estimates $\hat{x}_n$.
Rather than checking the value of $\lambda_n$, we may want to check the uncertainty by visual inspection of the informed-audiogram (see, step 15).

12. ELSE
13. compute best next stimulus:

$$s_{n+1}^* = \underset{s}{\operatorname{argmin}} \lambda_{n+1}(s)$$

In case the stopping criterion has not (yet) been met, we will present another pure-tone stimulus to the person tested. A pure-tone stimulus is a function of a chosen frequency and chosen power level. The set of possible frequencies and power levels defines the set of possible next stimuli. Having access to the full probability distribution $p(x|D_n)$ for the thresholds, makes it possible to select the stimulus s* from the set of all possible stimuli that provides the largest expected information gain (reduction of uncertainty). In particular, let $\lambda_{n+1}(d,s) = H[x|d,D_n]$ Hold the uncertainty estimate about the hearing thresholds, given audiometric observations $D_n$ and d. The expected information gain for a stimulus $s_{n+1}$ is then $$\lambda_{n+1}(s) = \sum_d p(d|s, D_n) H[x|d, D_n].$$

The best next stimulus, in the sense that it maximizes the expected information gain, is then given by $$s_{n+1}^* = \underset{s}{\operatorname{argmin}} \lambda_{n+1}(s).$$

14. Display informed-Audiogram $iA(\hat{x}_n, \lambda_n, s_{n+1}^*)$
At this point, after n hearing evaluation events, we have available a hearing threshold estimates $\hat{x}_n$, uncertainty measures $\lambda_n$ and the best next stimulus $s_{n+1}^*$. These three very informative variables are now displayed in a visualization graph that we call the informative-audiogram (abbreviated: i-audiogram), see FIG. 4. In a regular audiogram, hearing loss (in dB HL) is displayed on the ordinate axis versus frequency (in Hz) on the abscissa. In contrast, the i-audiogram displays, after the n-th stimulus-response event, the current best hearing threshold estimate $\hat{x}_n$ (32 in FIG. 4), the current uncertainty about the thresholds $\lambda_n$ (28/30 in FIG. 4, also indicated by the shaded region), and the best next stimulus $s_{n+1}^*$ (36 in FIG. 4). Note that the i-audiogram is updated after each response of the person tested. The i-audiogram provides a very informative picture about the current state of the estimation procedure.

15. audiologist chooses next stimulus: $s_{n+1}$

Next, based on the i-audiogram (and other not-simulated information), the audiologist may choose (and administer) the next pure-tone stimulus $s_{n+1}$. The audiologist will not necessarily be forced to select the 'optimal stimulus' $s_{n+1}*$. After all, there may be circumstances or constraints that the audiologist can but the computer simulation cannot take into account. Hence, the i-audiogram serves as an advisory system to the audiologist. In FIG. 4, we have indicated an example choice for $s_{n+1}$ by the '+'—sign—36. Expert intervention may be requested, since, while a statistically optimal estimation procedure will result from always choosing the 'optimal stimulus', an even faster and more accurate procedure may result from a deviating choice of the expert. Not all expert knowledge and information on the user's hearing loss can be coded into the hearing threshold model, and by presenting the uncertainty and suggested next stimulus we effectively combine expert knowledge with statistical optimality.

16. record response of the person tested $r_{n+1}$ and data $d_{n+1}=(r_{n+1},s_{n+1})$ Following presentation of the pure-tone stimulus $s_{n+1}$, the response (yes/no) of the person tested is recorded in $r_{n+1}$ and collected in the (n+1)-th data pair $d_{n+1}=(r_{n+1},s_{n+1})$.

17. n n+1

Figure 5:
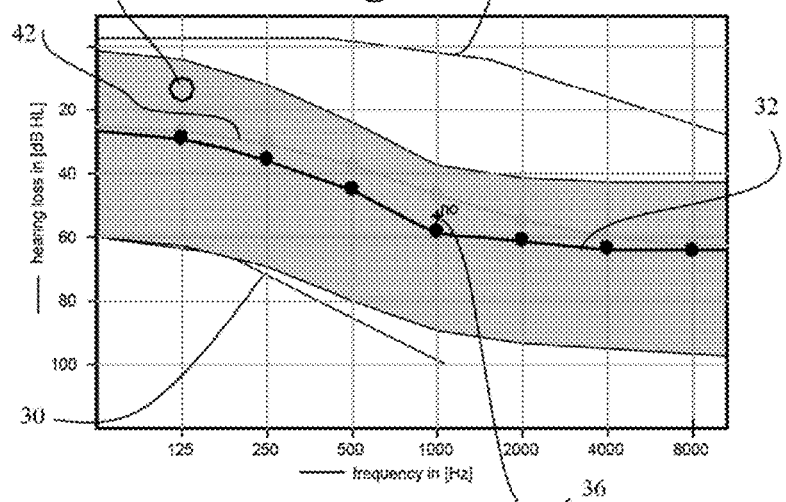
FIG. 5 is a schematic illustration of an audiogram.
Figure 6:
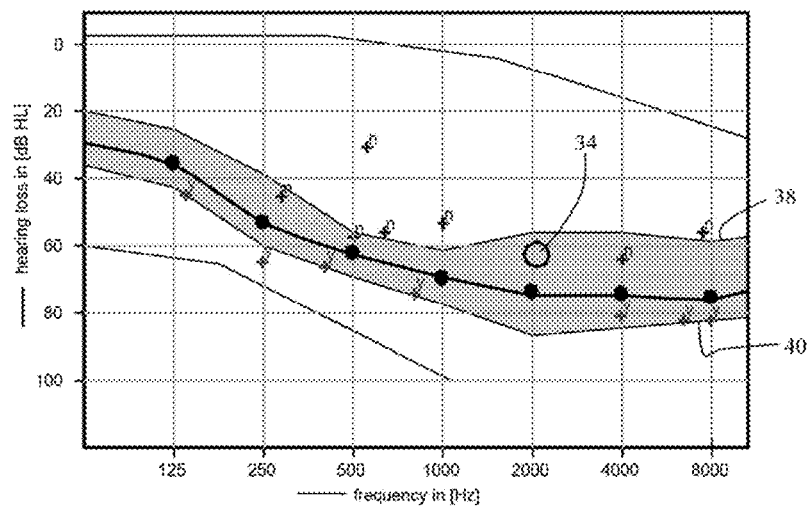
FIG. 6 is a schematic illustration of an audiogram.

The event index n is incremented by 1 and consequently, $d_n \leftarrow d_{n+1}$ in order to prepare for the estimation updates in the next iteration of the REPEAT loop. Assume now that the audiologist selected for $s_{n+1}$ where the '+'-sign is positioned in FIG. 4. Assume that the response of the person tested is 'no' (did not hear the stimulus). On the basis of this new information, the i-audiogram can be updated as shown in FIG. 5. We see that the current mean hearing threshold estimated shifted a bit downwards while the uncertainty about the thresholds decreased. Also, a new best next stimulus is indicated by the circle in FIG. 5. After a certain number of hearing evaluation events, the i-audiogram might look as shown in FIG. 6, where the threshold uncertainty has been drastically reduced on the basis of the newly obtained observations.

18. ENDIF

19. FOREVER

In one embodiment a representation of the probabilistic distribution of the hearing threshold for pure tones at different frequencies for a population of tested individuals (i.e. a representation of the hearing ability of a population), is provided as a mathematical model (i.e. a population model), specifically a Gaussian response curve, but alternative mathematical models also exist, which will have specific benefits depending on the nature of data for other response types than yes/no answers. In such an embodiment one benefit is that the combination of a representation of the hearing ability of a population with a single experimental observation of the response to a hearing evaluation event will provide estimates of multiple hearing ability values and their uncertainties.

In one embodiment, the probability distribution $p(\theta|D_n)$ is modeled by a hierarchical Bayesian model (see e.g. Rubin, T. N., Lee, M. D., & Chubb, C. F. (2008). Hierarchical Bayesian modeling of individual differences in texture discrimination. in V. Sloutsky, B. Love, & K. McRae (Eds.), *Proceedings of the* 30*th Annual Conference of the Cognitive Science Society*, pp. 1404-1409 Austin, Tex.: Cognitive Science Society) in order to divide subjects with similar hearing threshold patterns into groups. Effectively, this means that the individual responses in the population data are weighted according to their relevance for estimating the thresholds of the person tested.

An embodiment includes representing the probability distribution of the hearing ability values as a database of values. This is contemplated to have the benefit that no approximations will be made in the representation, but, compared to the use of a mathematical representation of the population of tested individuals, at the cost of a higher computing effort when experimental data is used as a lookup criterion to establish an estimate of multiple hearing ability values and their uncertainties.

In an embodiment the hearing evaluation event may include other stimuli such as masked speech. Masked speech is a combination of speech and noise which will indicate the speech hearing ability of the person being tested, as it is well known to the person skilled in the art. As the range of dependencies between e.g. masked speech and pure tone audiometry is high, it may be especially beneficial if a probabilistic representation involves both pure tone and speech related hearing ability values. For several types of hearing losses a correlation between left and right ear hearing ability will also mean that the use of binaural information, i.e. any information relating to the hearing ability of the other ear of the person tested, will be beneficial. A further related hearing loss ability value may be historical hearing ability values for the same person.

Such secondary parameters may either contribute explicitly to the mathematical models in order to minimize the uncertainty, or they may contribute by forming the basis of selection of sub-groups of the population, with a higher internal similarity, and thus a lower estimated uncertainty.

Embodiments also include the case where the hearing evaluation event includes registration of response in the form of electrical potentials related to the brain. In this embodiment the stimulus may simply be similar to that of other embodiments, or the stimulus may be of a more complex type such as frequency and/or amplitude modulated sound or tones.

An embodiment may include parameters known to correlate to hearing loss, without explicitly being related to a test of hearing loss. These parameters may include age, gender and medical status and history of the person tested, or a combination thereof. The parameters may either be used as model parameters, or for defining subsets of the population, matching the person tested better.

An embodiment may include improved determination of the most relevant hearing evaluation event for improving the estimation of a hearing ability value. By estimation of the objective function relating to the uncertainty of a hearing ability value the expected benefit (the expected information gain, i.e. the expected reduction of uncertainty) related to one or more hearing evaluation events may be estimated. The preferred next hearing evaluation event may be chosen, either automatically based on benefit, or manually by e.g. an audiologist operating the system. In the latter case an audiologist may also choose alternative hearing evaluation events, and the choice may be made freely, and/or after presentation of one or several estimates of the objective function.

An embodiment includes a step wherein inconvenience of different hearing events (such as the cost, the time or the practical inconvenience) is modeled in a cost model. The benefit of an estimated reduction of uncertainty of the audiogram and the cost of a proposed hearing evaluation event may then be balanced against each other in an objective function and the proceeding hearing evaluation event may be selected automatically or manually. Manual decisions by an audiologist may even be logged and used to automatically update objective function of the method.

An embodiment relates to a system comprising a data storage configured for storing the representation of the hearing ability of a population, a hearing evaluation device configured to perform the stimulus of a hearing evaluation event, a response registering device configured to register the response of the hearing evaluation event and a processor configured to establish a hearing ability model based on the representation of the hearing ability of the population and a observed response.

An embodiment relates to a system, wherein the estimated hearing ability value is displayed graphically together with a measure of uncertainty relating to the hearing ability value giving the operator an overview of the progress of the test. The graphical display is even more useful if the one or more preferred hearing events are presented together with the current observations.

An embodiment relates to a system implemented using a computer, comprising data storage configured for storing data regarding a representation of a hearing ability of a population, and a sound system configured to perform the stimulus of a hearing evaluation event, a mouse or keyboard configured to register the response of the hearing evaluation event and a processor configured to establish a hearing ability model based on the representation of the hearing ability of the population and a observed response. A computer screen may be used to display graphically one or more hearing ability value together with related measure of uncertainty. The hearing ability model may be stored in a medium (e.g., a volatile or a non-volatile medium).

In other embodiments, a computer product includes a medium that stores instruction, an execution of which by a processor causes a process to be performed, the process comprising obtaining data regarding a representation of a distribution of hearing ability for a population of individuals, obtaining information regarding a person's response to a stimulus of a hearing evaluation event, and establishing a hearing ability model representing a hearing ability of the person, based at least in part on the information and the representation of the distribution of the hearing ability for the population. A computer screen may be used to display graphically one or more hearing ability value together with related measure of uncertainty. The hearing ability model may be stored in a medium (e.g., a volatile or a non-volatile medium).

An embodiment includes use of a central database configured to communicate with other elements of the system via a communication system, such as the internet or any other data network. The central database may further receive contributions to the representation of the hearing ability of the population. The contributions may be used either directly as new data in the database, or alternatively, or in combination herewith, a central or local population model may be estimated from the revised data set. A method updating an estimated model from a previous model, and an additional data value will also be a possibility.

An embodiment of the method was implemented at the Sound and Image Processing laboratory at KTH, Stockholm. A Gaussian Mixture Model with 10 mixtures was trained as a probabilistic model $p(x|\theta)$ for the hearing thresholds with prior distribution $p(\theta|D_c)$, where the population data base $D_c$ comprised about 100,000 measured audiograms. The BIPTA procedure with optimal stimulus selection was applied to the estimation of hearing threshold patterns that were randomly drawn from the prior. On average, the BIPTA procedure needed 48 hearing evaluation events to get to an uncertainty of 2.9 dB, whereas the procedure according to the ASHA guideline above needed 135 events to reach the same uncertainty levels.

FIG. 4 schematically illustrates what could be displayed to an operator. In FIG. 4 the informative-audiogram before any hearing evaluation event is illustrated. The filled circles indicate the expected hearing thresholds at the test frequencies, here: 125, 250, 500, 1000, 2000, 4000, 8000 Hz, and connecting line the estimated thresholds at intermediate frequencies, i.e. the current values of the model. The shaded region indicates the current uncertainty about the hearing threshold values. The open circle indicates the best next pure-tone stimulus in the sense that this stimulus will maximize the expected information gain about the thresholds.

The illustration in FIG. 4 could be part of the first image displayed when a person is being examined. The lines 28 and 30 delimit the upper and lower boundaries indicating the uncertainty of the hearing loss in dB, the y-axis, at a given frequency, the x-axis. The lines 28 and 30 are determined based on population data, i.e. data from a large group of individuals. The population data may be established from a larger pool of data, e.g. by using selection criteria that may characterize the person being tested. Such criteria may for instance be age, gender, occupation, medical history. Examples could include military personnel who have suffered hearing loss due to gunfire, or women over 70 years of age or any other conceivable characteristics that may help establish a good starting point for the audiologist performing a hearing ability test. It is contemplated that the more the population data resembles the person tested the fewer hearing events are needed to establish a proper model for the hearing ability of that person tested.

Based on the population data a model 32 may be established. The model is illustrated by the solid line 32. The ring 34 represents the future listening event that is estimated to contribute the most to reducing the uncertainty of the model. The ring 34 serves as a guide to the audiologist, but the audiologist is free to choose any listening event that he or she whishes. The cross 36 represents the event that the audiologist has chosen.

FIG. 5 schematically illustrates an image that may follow the image of FIG. 4 after a further hearing evaluation event. The ring 34 again represents what the system determined as a suggestion, and the cross 36 illustrates the listening event that was chosen.

The lines 38 and 40 illustrate the updated boundaries for the uncertainty of the model after the listening event has been used to update the model. The updated model is illustrated by the solid dark line 32 and the previous model is illustrated by the dashed line 42.

Since the hearing thresholds at different frequencies are correlated and the method is designed to incorporate this correlation, the listening event 36 does not only have effect for the model at the precise frequency at which the event took place, but has relevance to the entire model. The closer the lines 38 and 40 are, the lower the uncertainty.

FIG. 6 schematically illustrates a situation where a number of listening events has been performed, here 14 listening events are illustrated. The lines 38 and 40 are significantly closer than illustrated in FIG. 5, indicating that the observations after the listening events have contributed to reducing the uncertainty. Also, the ring 34 indicating the event that is contemplated to contribute the most to reducing the uncertainty is provided.

Figure 7:
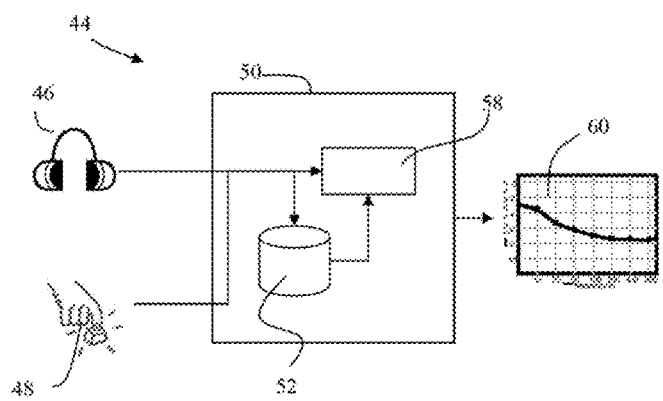
FIG. 7 is a schematic illustration of a system.

FIG. 7 is a schematic illustration of a system 44 comprising a sound emitting device 46 configured to emit sounds matching the desired stimuli of the hearing evaluation event.

An input device 48 (which may be a mouse, a keyboard, or combination thereof) communicates with a controller device 50 allowing a person to indicate if a particular sound signal was audible. The controller device 50 is configured to perform any or all steps described herein. The system 44 comprises a data storage 52. The data storage 52 comprises the population data used when establishing the model 60 for the hearing ability of the person by use of the processor 58. In some embodiments, parameters used by the processor 58 for determining the model, and/or the model itself, may also be stored in the data storage 52. The data storage 52 may be a volatile or non-volatile medium. Non-volatile media includes, for example, optical or magnetic disks. Volatile media includes dynamic memory. Also, in some embodiments, the system 44 includes a computer-readable medium having a set of stored instructions, an execution of which cases various function described herein to be performed. The term "computer-readable medium" as used herein refers to any medium that participates in providing instructions to the processor 58 for execution. Such a medium may take many forms, including but not limited to, non-volatile media and volatile media. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, or any other medium from which a computer can read.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

The invention claimed is:

1. A method of establishing an individual hearing ability model for a person using a representation of a distribution of hearing ability for a population of individuals, the method comprising:
    obtaining a probabilistic hearing ability model based on the representation of the distribution of the hearing ability for the population of individuals;
    obtaining information regarding the person's response to a stimulus of a hearing evaluation event; and
    updating, using a processor, the probabilistic hearing ability model to establish the individual hearing ability model for the person using the information regarding the person's response to the stimulus of the hearing evaluation event, wherein the probabilistic hearing ability model comprises a continuous function.

2. The method according to claim 1, wherein the act of updating is based at least in part on additional information regarding the person's additional response related to the hearing evaluation event or an additional hearing evaluation event.

3. The method according to claim 1, wherein the representation of the distribution of the hearing ability for the population of individuals comprises a mathematical population model.

4. The method according to claim 1, further comprising:
    determining an uncertainty relating to the individual hearing ability model based at least in part on the individual hearing ability model and the information.

5. The method according to claim 1, further comprising:
    determining at least one estimate of an objective function corresponding to at least one potential next hearing evaluation event based at least in part on the representation of the population.

6. The method according to claim 1, wherein the individual hearing ability model is established using Bayes rule.

7. The method according to claim 1, wherein the individual hearing ability model comprises one or more parameters.

8. The method according to claim 1, wherein the probabilistic hearing ability model is obtained using one or more parameters selected from the group consisting of age, gender, and medical history.

9. The method of claim 8, wherein the one or more parameters are included in the representation of the population.

10. The method according to claim 1, wherein the hearing evaluation event comprises a pure tone air conducted stimulation, a pure tone bone conducted stimulation, a masked pure tone stimulation, a masked speech stimulation, a modulated tone stimulation, or any combination thereof.

11. The method according to claim 1, wherein the information comprises a recording of an electrical potential related to a brain activity of the person.

12. The method of claim 1, wherein the continuous function comprises a continuous probability density function.

13. A system for establishing an individual hearing ability model of a hearing ability of a person, comprising:
    a data storage configured to store a representation of a distribution of a hearing ability of a population of individuals; and
    a processor configured to
        obtain a probabilistic hearing ability model based on the representation of the distribution of the hearing ability for the population of individuals,
        obtain information regarding the person's response to a stimulus of a hearing evaluation event, and
        updating the probabilistic hearing ability model to establish the individual hearing ability model for the person using the information regarding the person's response to the stimulus of the hearing evaluation event, wherein the probabilistic hearing ability model comprises a continuous function.

14. The system of claim 13, further comprising a device for performing the hearing evaluation event.

15. The system according to claim 13, further comprising a display device configured to display the individual hearing ability model, the stimulus, and the information.

16. The system according to claim 15, wherein the display device is further configured to display one or more preferred hearing evaluation events.

17. The system according to claim 13, further comprising a communication device configured to establish data communication to a remote data storage, wherein the remote data storage is configured to store data representing distribution of hearing ability of a plurality of hearing impaired individuals.

18. The system according to claim 13, further comprising a display device configured to display a hearing threshold audiogram, together with a related uncertainty and one or more preferred pure tone stimuli.

19. The system of claim 13, wherein the continuous function comprises a continuous probability density function.

20. A system for establishing an individual hearing ability model for a person using a representation of a distribution of hearing ability for a population of individuals, the system comprising:
   means for obtaining a probabilistic hearing ability model based on the representation of the distribution of the hearing ability for the population of individuals;
   means for obtaining information regarding the person's response to a stimulus of a hearing evaluation event; and
   means for updating the probabilistic hearing ability model to establish the hearing ability model for the person using the information regarding the person's response to the stimulus of the hearing evaluation event, wherein the probabilistic hearing ability model comprises a continuous function.

21. The system of claim 20, wherein the continuous function comprises a continuous probability density function.

22. A computer product having a non-transitory medium that stores instruction, an execution of which by a processor causes a process to be performed, the process comprising:
   obtaining a probabilistic hearing ability model based on a representation of a distribution of hearing ability for a population of individuals;
   obtaining information regarding a person's response to a stimulus of a hearing evaluation event; and
   updating the probabilistic hearing ability model to establish an individual hearing ability model for the person using the information regarding the person's response to the stimulus of the hearing evaluation event, wherein the probabilistic hearing ability model comprises a continuous function.

23. The computer product of claim 22, wherein the continuous function comprises a continuous probability density function.

24. A method of establishing an individual hearing ability model for a person using a representation of a distribution of hearing ability for a population of individuals, the method comprising:
   obtaining a probabilistic hearing ability model based on the representation of the distribution of the hearing ability for the population of individuals;
   obtaining information regarding the person's response to a stimulus of a hearing evaluation event; and
   updating, using a processor, the probabilistic hearing ability model to establish the individual hearing ability model for the person using the information regarding the person's response to the stimulus of the hearing evaluation event;
   wherein the individual hearing ability model for the person comprises an audiogram formed at least in part by an expected value of the updated probabilistic hearing ability model.

25. The method of claim 24, wherein the probabilistic hearing ability model comprises a hearing threshold probability function.

26. The method of claim 25, wherein the hearing threshold probability function comprises a hearing threshold probability density function.

27. The method of claim 25, wherein the hearing threshold probability function comprises a hearing threshold cumulative distribution function.

28. The method of claim 24, wherein the probabilistic hearing ability model comprises a continuous function.

29. A system for establishing an individual hearing ability model of a hearing ability of a person, comprising:
   a data storage configured to store a representation of a distribution of a hearing ability of a population of individuals; and
   a processor configured to
      obtaining a probabilistic hearing ability model based on the representation of the distribution of the hearing ability for the population of individuals;
      obtaining information regarding the person's response to a stimulus of a hearing evaluation event; and
      updating the probabilistic hearing ability model to establish the individual hearing ability model for the person using the information regarding the person's response to the stimulus of the hearing evaluation event;
      wherein the individual hearing ability model for the person comprises an audiogram formed at least in part by an expected value of the updated probabilistic hearing ability model.

30. The system of claim 29, wherein the probabilistic hearing ability model comprises a hearing threshold probability function.

31. The system of claim 30, wherein the hearing threshold probability function comprises a hearing threshold probability density function.

32. The system of claim 30, wherein the hearing threshold probability function comprises a hearing threshold cumulative distribution function.

33. The system of claim 29, wherein the probabilistic hearing ability model comprises a continuous function.

34. A method of establishing an individual hearing ability model for a person using a representation of a distribution of hearing ability for a population of individuals, the method comprising:
   obtaining a probabilistic hearing ability model based on the representation of the distribution of the hearing ability for the population of individuals, wherein the probabilistic hearing ability model comprises a continuous hearing threshold probability function;
   obtaining information regarding the person's response to a stimulus of a hearing evaluation event; and
   updating, using a processor, the hearing threshold probability function to establish the individual hearing ability model for the person using the information regarding the person's response to the stimulus of the hearing evaluation event.

35. The method of claim 34, wherein the individual hearing ability model for the person comprises an audiogram formed at least in part by an expected value of the updated hearing threshold probability function.

36. The method of claim 34, wherein the hearing threshold probability function comprises a hearing threshold probability density function.

37. The method of claim 34, wherein the hearing threshold probability function comprises a hearing threshold cumulative distribution function.

38. A system for establishing an individual hearing ability model of a hearing ability of a person, comprising:

a data storage configured to store a representation of a distribution of a hearing ability of a population of individuals; and a processor configured to obtaining a probabilistic hearing ability model based on the representation of the distribution of the hearing ability for the population of individuals, wherein the probabilistic hearing ability model comprises a continuous hearing threshold probability function;

obtaining information regarding the person's response to a stimulus of a hearing evaluation event; and updating, using a processor, the hearing threshold probability function to establish the individual hearing ability model for the person using the information regarding the person's response to the stimulus of the hearing evaluation event.

39. The system of claim 38, wherein the individual hearing ability model for the person comprises an audiogram formed at least in part by an expected value of the updated hearing threshold probability function.

40. The system of claim 38, wherein the hearing threshold probability function comprises a hearing threshold probability density function.

41. The system of claim 38, wherein the hearing threshold probability function comprises a hearing threshold cumulative distribution function.

* * * * *